(12) United States Patent
Eigler et al.

(10) Patent No.: US 6,328,699 B1
(45) Date of Patent: Dec. 11, 2001

(54) PERMANENTLY IMPLANTABLE SYSTEM AND METHOD FOR DETECTING, DIAGNOSING AND TREATING CONGESTIVE HEART FAILURE

(75) Inventors: Neal L. Eigler, Pacific Palisades; James S. Whiting, Los Angeles, both of CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 0 days.

(21) Appl. No.: 09/481,084

(22) Filed: Jan. 11, 2000

(51) Int. Cl.$^7$ .................................................. A61B 5/02
(52) U.S. Cl. .................... 600/486; 600/485; 600/508
(58) Field of Search .................................. 600/486, 485, 600/488, 508

(56) References Cited

U.S. PATENT DOCUMENTS

| | | | |
|---|---|---|---|
| 4,899,751 | * | 2/1990 | Coehn .................................... 600/486 |
| 4,899,752 | * | 2/1990 | Cohen .................................... 600/486 |
| 4,899,758 | | 2/1990 | Finkelstein et al. . |
| 4,967,749 | | 11/1990 | Cohen . |
| 5,103,828 | | 4/1992 | Sramek . |
| 5,163,439 | | 11/1992 | Cohen . |
| 5,190,528 | | 3/1993 | Fonger et al. . |
| 5,314,418 | | 5/1994 | Takano et al. . |
| 5,368,040 | | 11/1994 | Carney . |
| 5,398,692 | | 3/1995 | Hickey . |
| 5,464,434 | | 11/1995 | Alt . |
| 5,498,524 | | 3/1996 | Hall . |
| 5,535,752 | | 7/1996 | Halperin et al. . |
| 5,743,267 | | 4/1998 | Nikolic et al. . |
| 5,752,976 | | 5/1998 | Duffin et al. . |
| 5,758,652 | | 6/1998 | Nikolic . |
| 5,861,018 | | 1/1999 | Feierbach . |
| 5,904,708 | | 5/1999 | Goedeke . |
| 5,919,210 | | 7/1999 | Lurie et al. . |
| 5,921,935 | * | 7/1999 | Hickey ................................. 600/485 |
| 6,223,081 | | 4/2001 | Kerver . |
| 6,223,087 | | 4/2001 | Williams . |
| 6,234,973 | | 5/2001 | Meador et al. . |

FOREIGN PATENT DOCUMENTS

| | | |
|---|---|---|
| 0 472 411 A1 | 2/1992 | (EP) . |
| 1 050 265 A2 | 11/2000 | (EP) . |
| 1 057 448 A1 | 12/2000 | (EP) . |
| WO 96/11722 | 4/1996 | (WO) . |
| WO 99/56812 | 11/1999 | (WO) . |

OTHER PUBLICATIONS

Steinhaus, David M. et al., Intitial Experience with an Implantable Hemodynamic Monitor, *Circulation*, vol. 93, No. 4, pp. 745–752 (Feb. 15, 1996).

Soufer, Robert, Treating a Sick Heart, *Heart Disease*, Nova Online web page (copyright 1997, WGBH).

Neergaard, Lauran, *Internet assists in daily heart monitoring*, CNN.com health web page: Feb. 22, 2000, (copyright 2000, Cable News Network).

\* cited by examiner

*Primary Examiner*—John P. Lacyk
*Assistant Examiner*—Navin Natnithithadha
(74) *Attorney, Agent, or Firm*—Knobbe, Martens, Olson & Bear, LLP

(57) ABSTRACT

The invention provides improved apparatus and methods for treating congestive heart failure in a medical patient. The apparatus includes a pressure transducer permanently implantable within the left atrium of the patient's heart and operable to generate electrical signals indicative of fluid pressures within the patient's left atrium. The pressure transducer is connected to a flexible electrical lead, which is connected in turn to electrical circuitry, which in the preferred embodiment includes digital circuitry for processing electrical signals. The electrical circuitry processes the electrical signals from the pressure transducer and, based at least in part on those signals, generates a signal that indicates a desired therapeutic treatment for treating the patient's condition. That signal is then communicated to the patient via a patient signaling device, following which the patient administers to him or herself the prescribed therapeutic treatment indicated by the signal.

143 Claims, 9 Drawing Sheets

US 6,328,699 B1

PERMANENTLY IMPLANTABLE SYSTEM AND METHOD FOR DETECTING, DIAGNOSING AND TREATING CONGESTIVE HEART FAILURE

BACKGROUND OF THE INVENTION

Heart failure is a condition in which a patient's heart works less efficiently than it should, a condition in which the heart fails to supply the body sufficiently with the oxygen rich blood it requires, either at exercise or at rest. Congestive heart failure (CHF) is heart failure accompanied by a build-up of fluid pressure in the pulmonary blood vessels that drain the lungs. Transudation of fluid from the pulmonary veins into the pulmonary interstitial spaces, and eventually into the alveolar air spaces, is called pulmonary edema, and can cause shortness of breath, hypoxernia, acidosis, respiratory arrest, and death.

It is estimated that about four million people in the United States suffer from various degrees of heart failure. Although CHF is a chronic condition, the disease often requires acute hospital care. Patients are commonly admitted for acute pulmonary congestion accompanied by serious or severe shortness of breath. Acute care for congestive heart failure accounts for the use of more hospital days than any other cardiac diagnosis, and consumes in excess of seven and one-half billion dollars in the United States annually.

It is far more cost effective, and much better for the patient's health, if chronic CHF can be managed and controlled by the routine administration of appropriate drug therapy rather than by hospital treatment upon the manifestation of acute symptoms. Patients with chronic CHF are typically placed on triple or quadruple drug therapy to manage the disease. The drug regimen commonly includes diuretics, vasodilators such as ACE inhibitors or A2 receptor inhibitors, and inotropic agents usually in the form of cardiac glycosides such as Digoxin. Patients may also be placed on beta blockers such as Carvedilol.

As with all drugs, these agents must be taken in doses sufficient to ensure their effectiveness. Problematically, however, over-treatment can lead to hypotension, renal impairment, hyponatremia, hypokalemia, worsening CHF, impaired mental functioning, and other adverse conditions. Adding to the challenge of maintaining proper drug dosage is the fact that the optimal dosage will depend on diet, particularly salt and fluid intake, level of exertion, and other variable factors. Adding further to the problem of managing this condition is the fact that patients frequently miss scheduled doses by forgetting to take pills on time, running out of medications, or deciding to stop medications without consulting their physician. It is important, therefore, that the patient's condition be monitored regularly and thoroughly, so that optimal or near optimal drug therapy can be maintained. This monitoring is itself problematic, however, in that it requires frequent visits with a caregiver, resulting in considerable inconvenience and expense.

It would be highly advantageous, therefore, if methods and apparatus could be devised by which a patient's congestive heart failure could be monitored routinely or continuously with minimal attendance by a caregiver, and then only when actually required. It would be further advantageous if such methods and apparatus included means for communicating diagnostic information not only to the physician but to the patient himself, so that the patient could continue or modify his own drug therapy appropriately and generally without the direct intervention of a physician. The present invention provides these very advantages, along with others that will be further understood and appreciated by reference to the written disclosure, figures, and claims included in this document.

SUMMARY OF THE INVENTION

The invention provides improved apparatus and methods for treating congestive heart failure in a medical patient. The apparatus includes a pressure transducer permanently implantable within the left atrium of the patient's heart and operable to generate signals indicative of fluid pressures within the patient's left atrium. The pressure transducer is connected in turn to signal processing apparatus, which in the preferred embodiment includes digital circuitry for processing electrical signals. The signal processing apparatus processes the electrical signals from the pressure transducer and, based at least in part on those signals, generates a signal that indicates a desired therapeutic treatment for treating the patient's condition. That signal is then communicated to the patient via a patient signaling device, following which the patient administers to him or herself the prescribed therapeutic treatment indicated by the signal.

BRIEF DESCRIPTION OF THE DRAWINGS

The structure and operation of the invention will be better understood with the following detailed description of preferred embodiments of the invention, along with the accompanying illustrations, in which.

DESCRIPTION OF THE PREFERRED EMBODIMENTS

The invention provides a system for continuously or routinely monitoring the condition of a patient suffering from chronic congestive heart failure (CHF). As will be described in detail below, a system incorporating the invention monitors the patient's left atrial pressure, and, depending upon the magnitude of or changes in this pressure, the system communicates a signal to the patient indicative of a particular course of therapy appropriate to manage or correct, as much as possible, the patient's chronic condition.

Elevating pressure within the left atrium of the heart is the precursor of fluid accumulation in the lungs which is symptomatic of acute CHF. Means left atrail pressure in healthy individuals in normally less than about twelve millimeters of mercury (mm Hg). Patients with CHF who have been medically treated and clinically "well compensated" may generally have mean left atrail pressures in the range from fifteen to twenty mm Hg. Transudation of fluid into the pulmonary interstitial spaces can be expected to occur when the left atrial pressure is about twenty-five mm Hg, or at somewhat more than about thirty mm Hg in some patients with chronic CHF. Pulmonary edema has been found to be very reliable predicted by reference to left atrial pressures, and much less well correlated with conditions in any other chamber of the heart Thus, the methods and apparatus of the invention are expected to prove very useful in treating and preventing pulmonary edema and other adverse conditions associated with CHF.

A system according to the invention includes a pressure sensor that is implanted within the patient and positioned to measure pressures within the patient's left atrium. Signals from the pressure sensor are monitored continuously or at appropriate intervals. Physician-programmed coded communications are then transmitted to the patient corresponding to appropriate drug therapies that the patient may in most cases administer to him or herself without further diagnostic intervention from a physician.

Figure 1:
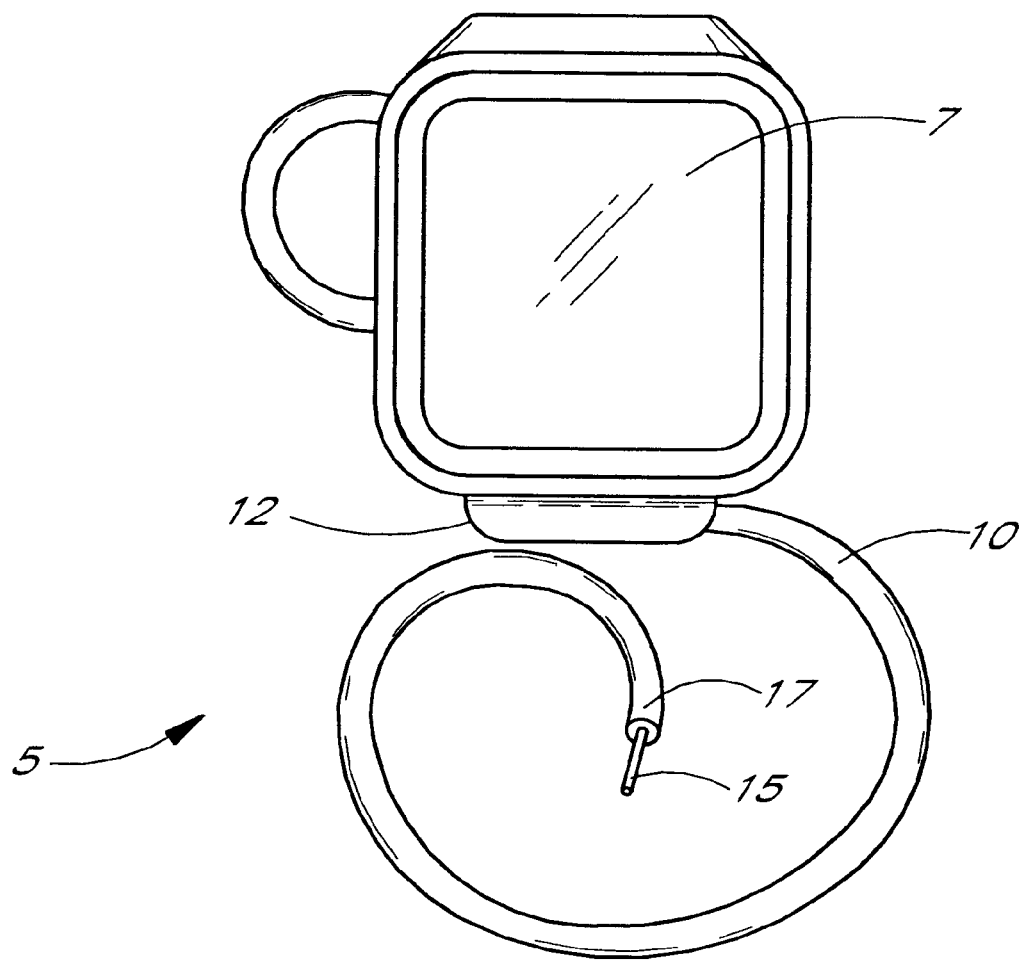
FIG. 1 depicts apparatus suitable for practicing the invention.

Apparatus 5 for practicing the invention is depicted in FIG. 1. The apparatus comprises a housing 7 and a flexible, electrically conductive lead 10. The lead is electrically connectable to the housing through a connector 12 on the exterior of the housing. The housing is outwardly similar to the housing of an implantable electronic defibrillator system. Defibrillator and pacemaker systems are implanted routinely in medical patients for the detection and control of tachy- and bradyarrythmias.

The flexible lead 10 is also generally similar to leads used in defibrillator and pacemaker systems, except that a compact pressure transducer 15 is disposed at the distal end 17 of the lead, opposite the connector 12 on the housing 7. The pressure transducer measures fluid pressure in its immediate vicinity. An electrical signal or another form of signal indicative of this pressure is then transmitted along the lead through the connector and from there to circuitry inside the housing.

The left atrium can be accessed from the right atrium through the atrial septum separating the right and left atria. The flexible lead 10 and pressure transducer 15 will be anchored to the atrial septum. This placement can be achieved using vascular access techniques that are well-known to those familiar with the performance of invasive cardiovascular procedures, and in particular to interventional cardiologists and cardiovascular surgeons. These procedures are commonly performed with the aid of visualization techniques including standard fluoroscopy, cardiac ultrasound, or other appropriate visualization techniques used alone or in combination.

Access to the central venous circulation may be achieved by use of the standard Seldinger technique through the left or right subclavian vein, the right or left internal jugular vein, or the right or left cephalic vein. Alternatively, access may be made via the Seldinger technique into the right femoral veins. In either case, Brockenbrough catheter and needle are used to pierce the atrial septum for access to the left atrium.

Figure 2:
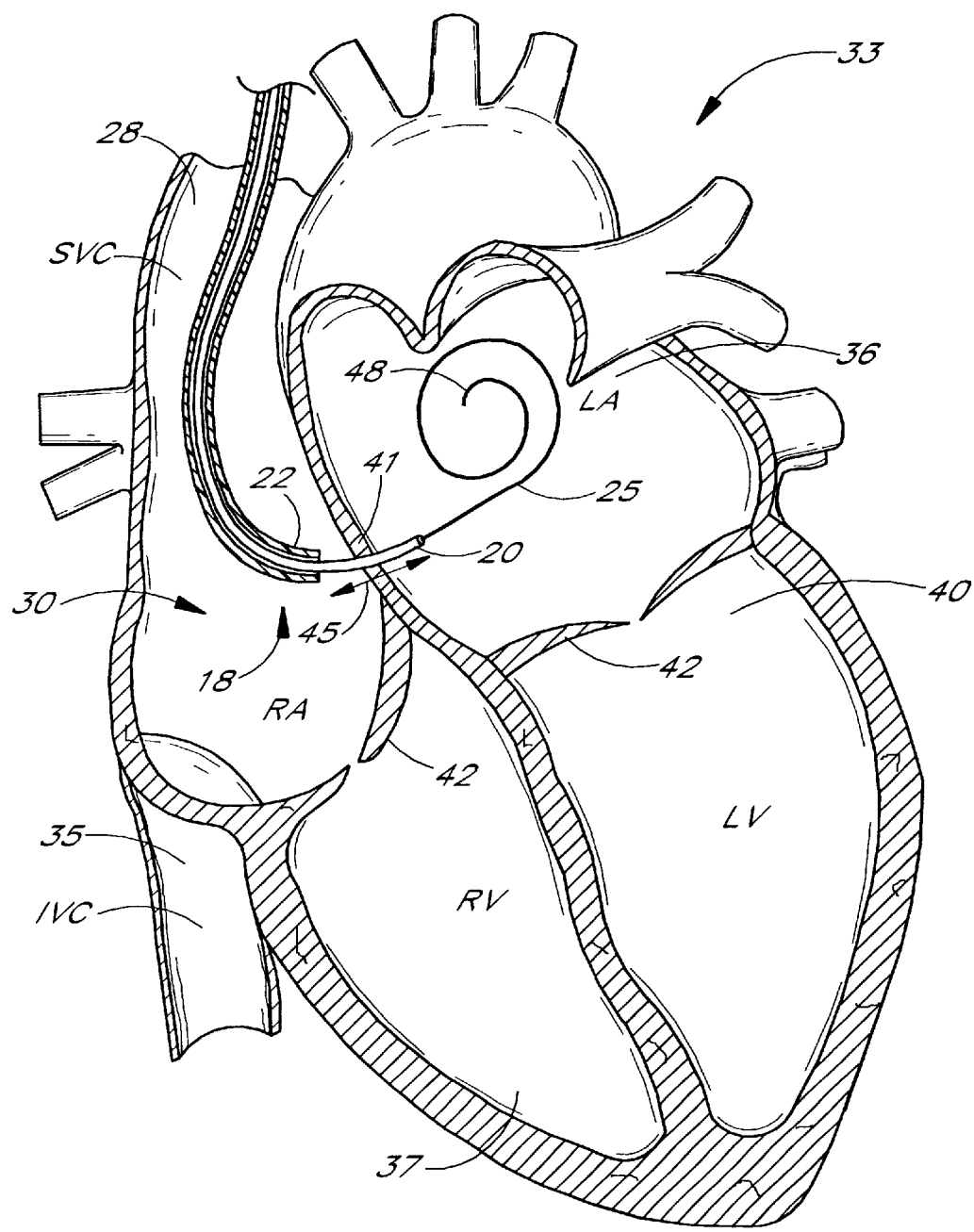
FIG. 2 is a schematic sectional view of a patient's heart showing a part of the apparatus of the invention positioned therein.

FIG. 2 provides a schematic sectional view of the patient's heart and shows the apparatus used to access the left atrium. FIG. 2 depicts an access assembly 18 comprising a Brockenbrough catheter 20 inside a peel-away sheath 22, with a flexible guidewire 25 residing within the Brockenbrough catheter. As FIG. 2 indicates, the access assembly has been placed through the superior vena cava 28 into the right atrium 30 of the heart 33. FIG. 2 shows as well the inferior vena cava 35, the left atrium 36, the right ventricle 37, the left ventricle 40, the atrial septum 41 that divides the two atria, and the valves 42 between the right atrium and right ventricle, and the left atrium and left ventricle. The reader will appreciate that the view of FIG. 2 is simplified and somewhat schematic, but that nevertheless FIG. 2 and the other views included herein will suffice to illustrate adequately the placement and operation of the present invention.

With the access assembly 18 in place within the right atrium 30, the Brockenbrough catheter 20 is used to pierce the atrial septum 41 by extending the Brockenbrough needle (not shown) through the atrial septum into the left atrium 36. In the figures, the atrial septum has been pierced by the needle, the catheter 20 advanced over the needle, and the needle withdrawn from the catheter leaving the catheter in place inside the left atrium. Optionally, a guidewire may be advanced through the needle into the left atrium before or after advancing the catheter, or it may be placed into the left atrium through the catheter alone after the needle has been withdrawn.

As indicated by the arrows 45 in FIG. 2, the peel-away sheath 22 may extend into the left atrium, or it may remain on the near side of the atrial septum within the right atrium 30. FIG. 2 shows the guidewire 25 extended from the end of the Brockenbrough catheter to secure continuous access into the left atrium. As depicted therein, the guidewire has a curled, "pig-tail" style distal tip 48 to better secure the guidewire within the left atrium and to safeguard against inadvertent withdrawal through the atrial septum. Once the guidewire is in place in the left atrium, the Brockenbrough catheter is withdrawn so that the flexible lead 10 (see FIG. 3) may be placed through the peel-away sheath 22.

The reader may appreciate that the configuration shown in FIG. 2 is one that results from an approach from the superior venous circulation through the superior vena cava. If the approach is made from the inferior venous circulation through an entry into the right femoral vein, access into the right atrium 30 will be made via the inferior vena cava 35.

If the approach is made from the inferior venous circulation, an additional procedure is required to transfer the proximal end of the guidewire to the superior venous circulation after its distal end has been placed into the left atrium. This must be done to allow the sensor and its lead to be inserted over the guidewire from a superior vein into the left atrium. One method for transferring the proximal end of the guidewire from an inferior to a superior vein is to use a guidewire that has a preformed bend somewhere along its central body. After the atrial septum 41 is penetrated and the distal tip of the guidewire placed in the left atrium 36, the Brockenbrough catheter and sheath are withdrawn to a point just proximal of the guidewire bend. Then, with care being used to maintain the distal tip of the guidewire in place in the left atrium, the needle and sheath are used to push the central body of the guidewire into the superior venous circulation. A guidewire hook (not shown) may then be used to retrieve the guidewire body through an access sheath placed into the superior venous system so that the proximal end of the guidewire extends out of the patient through the patient's superior venous circulation.

Either approach described above results in the placement of a guidewire with its distal tip in the left atrium 36 and extending (in the proximal direction) through the atrial septum 41, the right atrium 30, the superior vena cava 28, and out of the patient's body through a superior venous access site. These approaches are generally conventional and widely known in the medical arts. While neither is a trivial procedure, they are both well within the capabilities of a skilled interventional cardiologist, radiologist, vascular or cardiac surgeon, or a similarly skilled medical practitioner.

With the guidewire 25 securely in place with its distal tip 48 inside the left atrium 36, the flexible lead 10 may be advanced into the left atrium. The flexible lead might itself include a central lumen configured to receive the proximal end of the guidewire, thereby allowing the flexible lead to be advanced down the guidewire toward the left atrium. More commonly, an exchange catheter, which may be in the form of a peel-away sheath 22, will be advanced down the guidewire and placed into the left atrium, after which the flexible lead will be advanced down the exchange catheter and into position. Once the pressure transducer of the flexible lead is positioned within the left atrium, the lead should be anchored in place to ensure that the pressure transducer stays reliably and permanently in the desired location.

Figure 3:
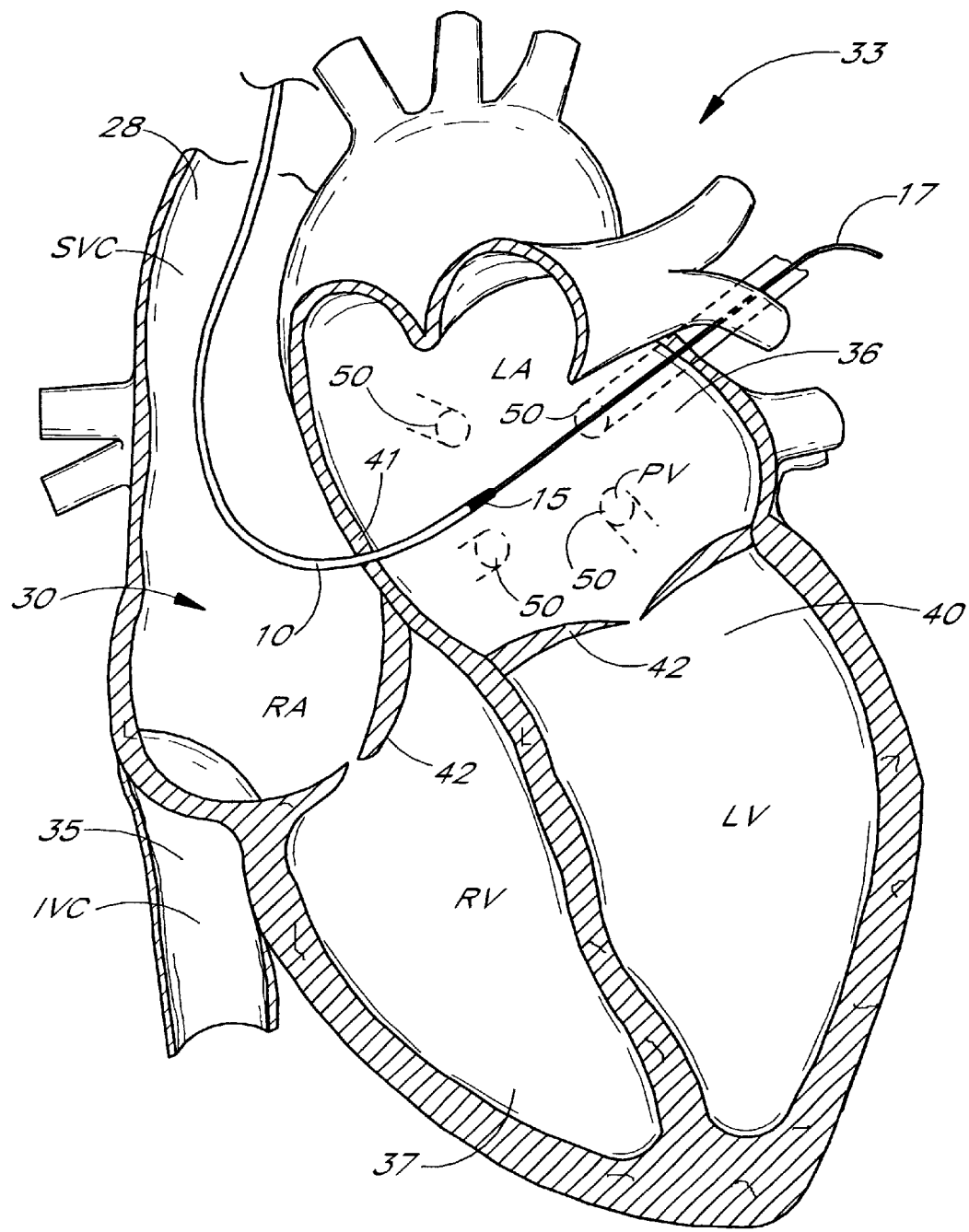
FIG. 3 depicts a method for anchoring within the patient's heart a flexible electrical lead that comprises a part of the apparatus for practicing the invention.

One method for anchoring the flexible lead 10 in place is depicted in FIG. 3, which is like FIG. 2 a somewhat schematic depiction of some of the major structures of the heart. FIG. 3 shows the four pulmonary veins 50 that connect to the left atrium 36. In the particular apparatus depicted in FIG. 3, the flexible lead 10 includes a pressure transducer 15 located on the body of the lead a short distance proximal of the distal end 17 of the lead.

As FIG. 3 indicates, the distal end 17 of the flexible lead 10 in this embodiment can be bent by the operator in much the same way as a distal tip such as might be found on a steerable angioplasty guidewire or another similar device. This feature assists the operator in steering the flexible lead into a selected one of the pulmonary veins 50, with the pressure transducer 15 disposed within the interior space of the left atrium 36, or even within the pulmonary vein itself. Placement of the pressure transducer within the pulmonary vein is effective because pressures within the pulmonary vein are very close to pressures within the left atrium. It will be appreciated by those skilled in the art that visualization markers (not shown) may be provided at appropriate locations on the flexible lead to assist the operator in placing the device as desired. With the flexible lead in place as shown, the body's own natural healing mechanism will permanently anchor the flexible lead in place both at the penetration site through the atrial septum 41, and where the flexible lead contacts the interior surface of the pulmonary vein in which the tip of the lead resides. The pressure transducer might also be placed at locations such as the left atrial appendage or the left ventricular cavity, regions in which pressures are nearly the same as pressures in the left atrium.

Figure 4:
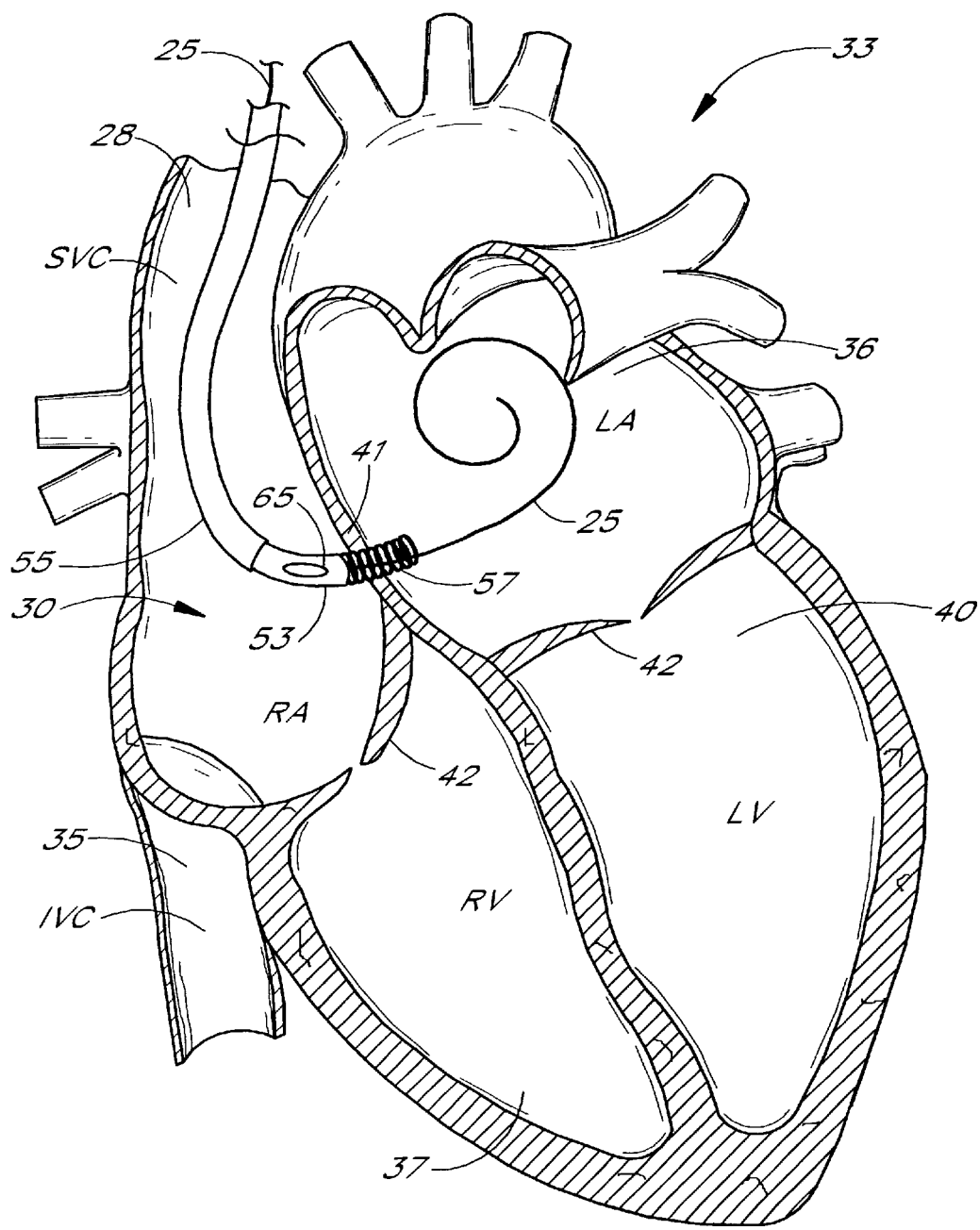
FIG. 4 shows an alternative method for anchoring a lead within the heart, including a helical screw for advancement into the patient's atrial septum.
Figure 5:
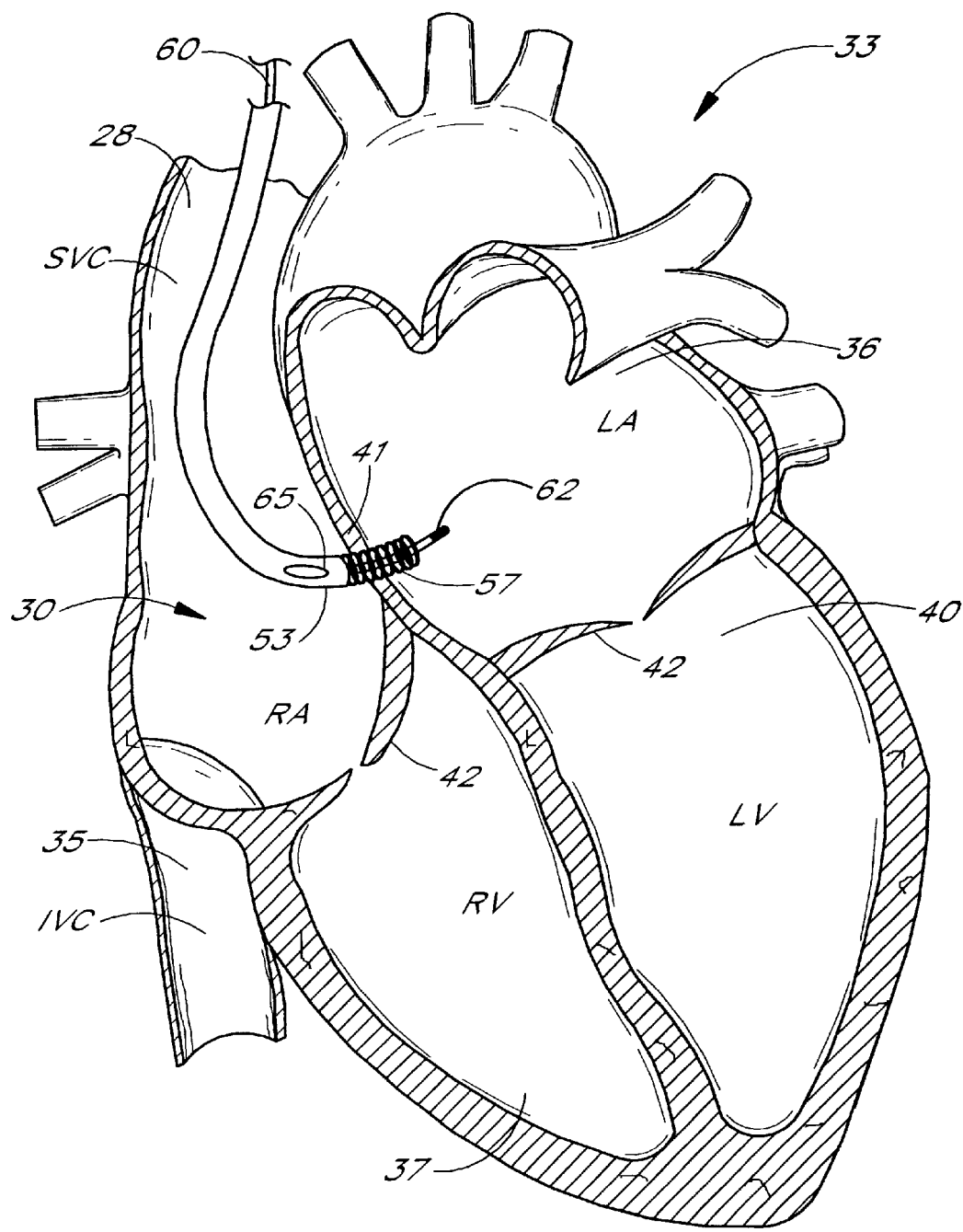
FIG. 5 shows the apparatus depicted in FIG. 4, with a pressure sensing transducer in place in the patient's left atrium.

FIGS. 4 and 5 show alternative means for anchoring the pressure transducer in a location appropriate for measuring pressures within the left atrium 36. The lead in this embodiment includes a helical screw thread for anchoring the lead to the atrial septum 41. Similar configurations are used in some leads for pacemakers and thus may be familiar to those skilled in the art.

Referring now specifically to FIG. 4, the guidewire 25 is shown positioned across the atrial septum 41 between the right atrium 30 and the left atrium 36. A first lead component 53 is delivered over the guidewire through an appropriate guiding catheter 55 or sheath. This first lead component includes a helical screw 57 on its exterior surface. The helical screw is advanced into the tissue of the atrial septum by applying torque to the shaft of the first lead component. The helical screw could also be coupled to a hollow or solid cylindrical mandrel (not shown), or to a spirally wound mandrel (also not shown) disposed along substantially the entire length of the first lead component. When the helical screw has been turned and advanced sufficiently into the atrial septum, the guidewire and guiding catheter may then be withdrawn leaving the first lead component anchored securely in place.

With the guidewire having removed, a second lead component 60 is advanced as shown in FIG. 5 through the central lumen of the first lead component 53. The first and second lead components are sized and configured so that when the second lead component is fully advanced with respect to the first lead component, a left atrial pressure transducer 62 at the end of the second lead component protrudes by an appropriate predetermined amount into the left atrium 36. The second lead component is then securely fixed with respect to the first lead component.

It should be noted that the embodiment depicted in FIGS. 4 and 5 includes a second pressure transducer 65 on the exterior of the first lead component 53 and exposed to pressure within the right atrium 30. This illustrates in a simplified way a general principle of the invention, in which a pressure transducer is used to measure fluid pressure within the left atrium, but in which one or more additional transducers or sensors may also be used to detect a physiologic condition other than left atrial pressure. These physiologic conditions may include pressures in locations other than the left atrium 36, and physical parameters other than pressure, either within the left atrium or at other locations.

Figure 6:
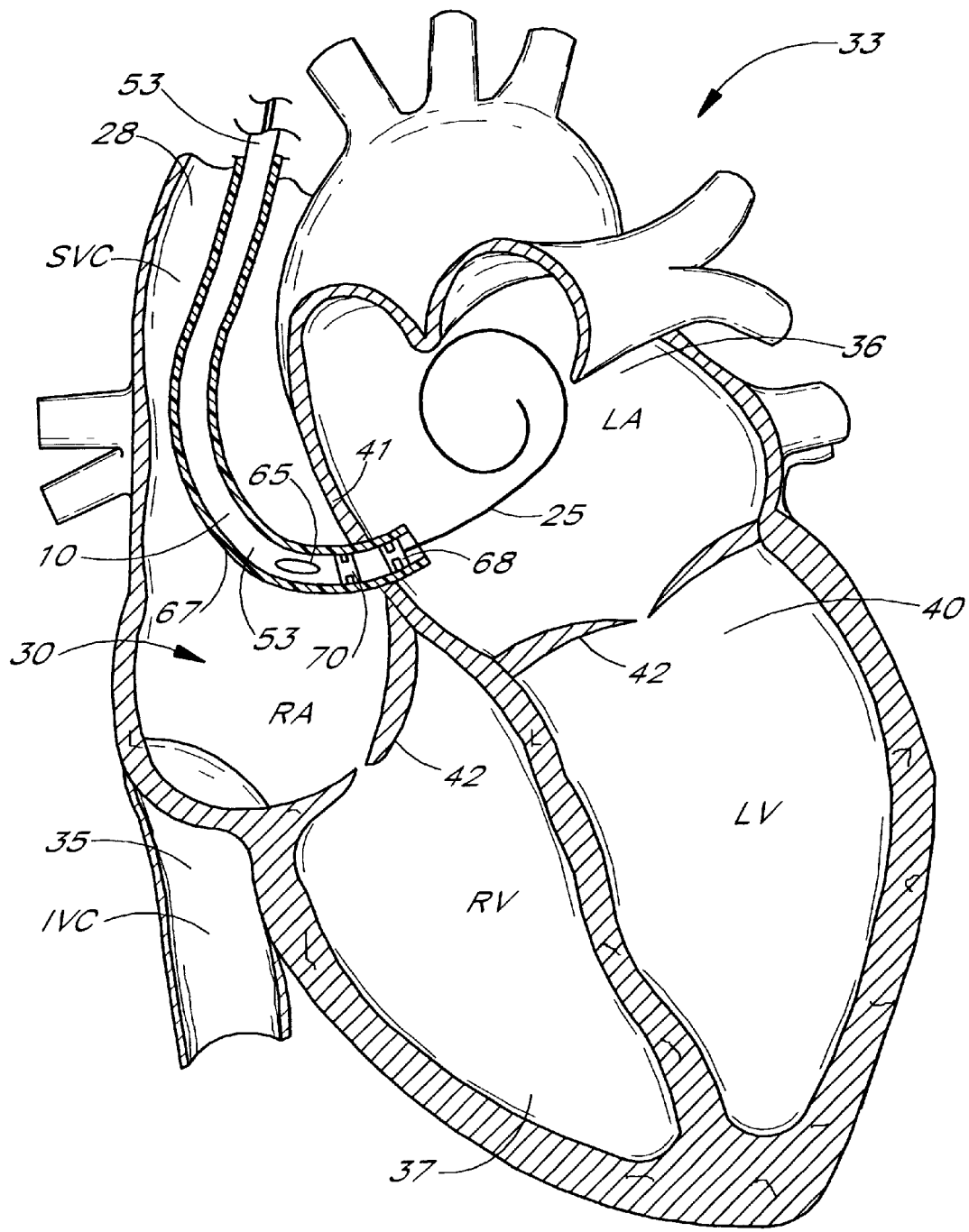
FIG. 6 depicts a flexible lead including deployable anchors carried inside a removable sheath and placed through the atrial septum.
Figure 7:
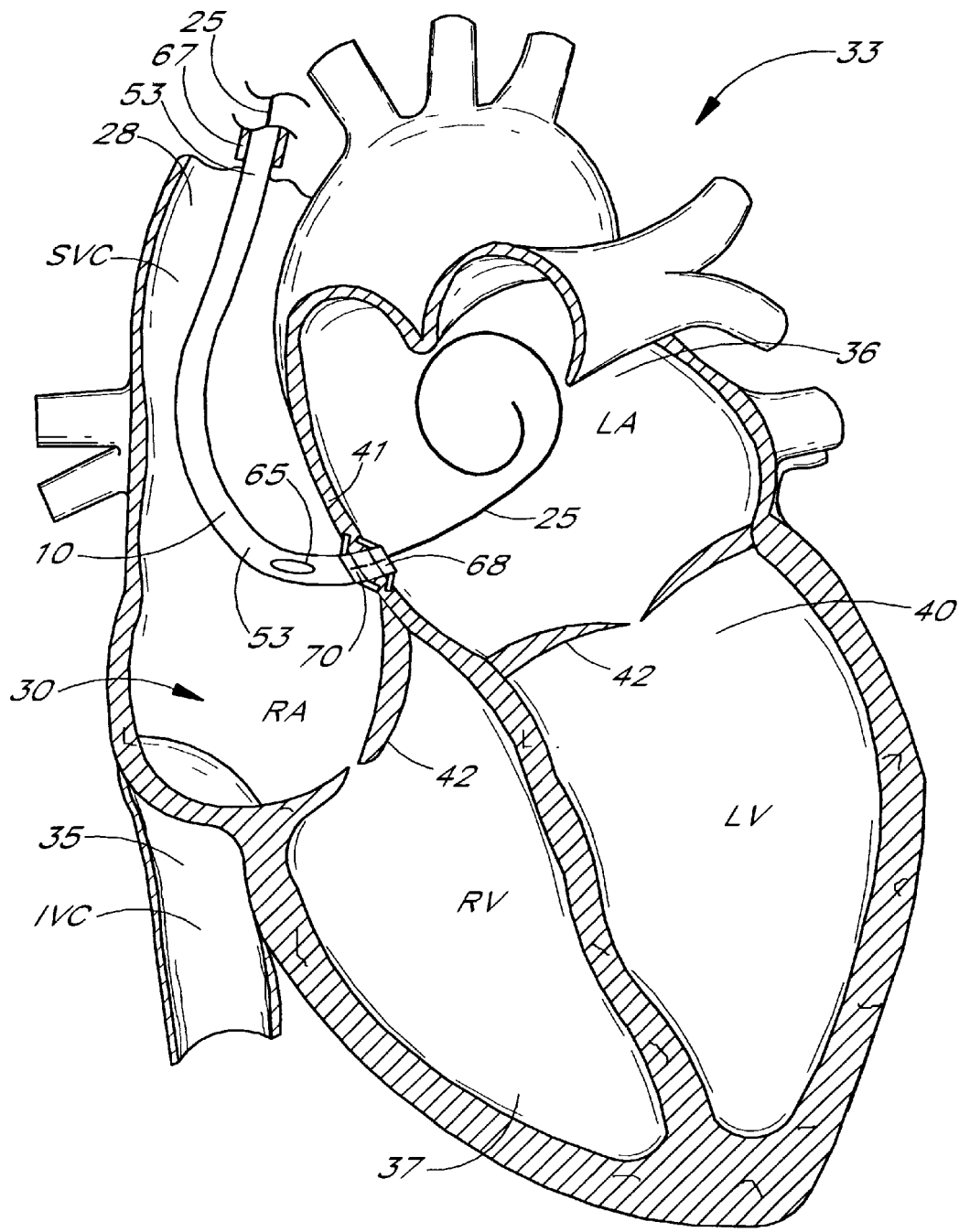
FIG. 7 shows the flexible lead of FIG. 6 with the sheath withdrawn to deploy the anchors on opposite sides of the atrial septum.
Figure 8:
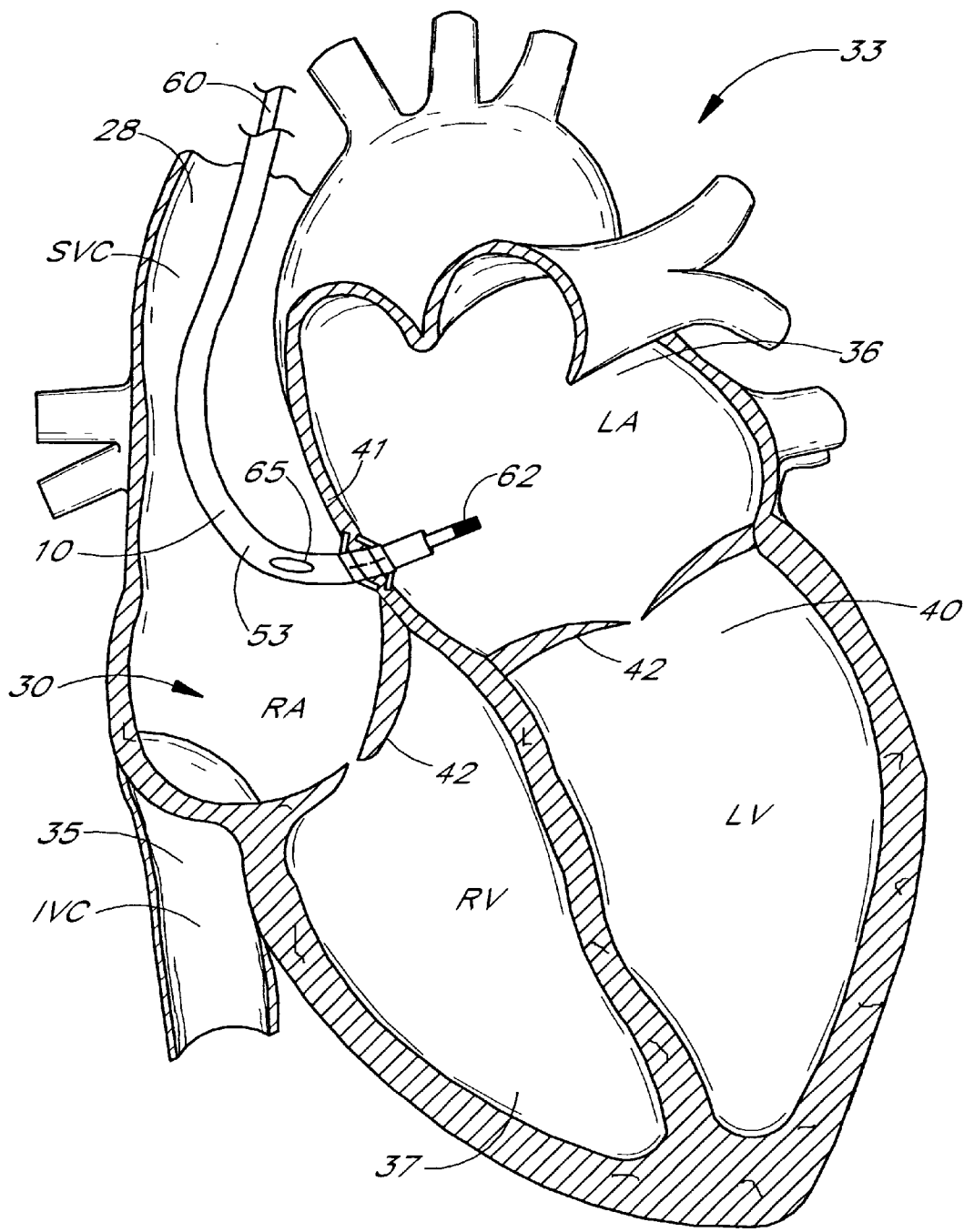
FIG. 8 shows the flexible lead of FIGS. 6 and 7, with a pressure sensing transducer in place inside the patient's left atrium.

FIGS. 6, 7, and 8 show another embodiment of a flexible lead 10 suitable for use with the invention, in which folding spring-like fins or anchors deploy to anchor the lead in place in the atrial septum 41. Referring specifically to FIG. 6, a first lead component 53 is advanced through a sheath 67, the sheath having been advanced across the atrial septum. In this embodiment, the first lead component includes folding distal anchors 68 and proximal anchors 70, which lie folded and are held in place inside the interior lumen of the sheath. When the first lead component and sheath are properly positioned, which will generally involve the use of fluoroscopy or an alternative technique for imaging, the operator may carefully withdraw the sheath from around the first lead component. As the distal and proximal anchors exit the sheath, they deploy themselves (as depicted in FIG. 7) on either side of the atrial septum, thereby anchoring the first lead component securely in place. Similar anchors are sometimes used with leads for pacemakers and other medical devices where permanent anchoring is desired, and the operation of these anchors will thus be not entirely unfamiliar to the knowledgeable reader.

Referring now on FIG. 8, a second lead component 60 is advanced through a central lumen of the first lead component 53 after the guidewire 25 (see FIGS. 6 and 7) and sheath 67 are removed. As i the previous embodiment, a left atrial pressure transducer 62 is carried at the distal end of the second lead component. Again the first and second lead components are sized and configured with respect to one another so that the left atrial pressure transducer protrudes from the first lead component an appropriate amount into the left atrium 36. Also as in the previous embodiment, a second pressure transducer 65 on the exterior of the first lead component allows for the measurement and transmittal of pressure within the right atrium 30.

Alternative systems and methods have been described for anchoring a flexible lead with a pressure transducer disposed to measure pressure within the patient's left atrium. Other anchoring methods may be devised by those skilled in the relevant arts without departing in any way from the principles of the invention. Moreover, approaches have been described by which the lead is positioned between the left atrium and an exit site from the to patient's superior venous circulation. Alternate lead routes and exit sites may find use as well.

Referring back to FIG. 1, an exit from the superior venous system is advantageous because, with the flexible lead 10 connected to the housing 7 via the connector 12, the housing may be surgically implanted into the patient's body, typically in a subcutaneous pocket, which may be formed, e.g., in the shoulder area in proximity to the patient's clavicle, in a manner quite similar to that routinely performed to implant pacemakers and implantable cardiac defibrillators. The device described herein may thus be implanted and operational within the patient's body for extended periods.

Coaxial lead configurations as described, in which a central lead portion carrying a sensor is inserted in an outer lead portion carrying anchoring apparatus after the anchoring apparatus is deployed, are advantageous for a number of reasons. First, the lead portion carrying the anchoring apparatus is advanced to the target site over a guidewire, which remains in place until the anchoring apparatus is securely deployed. If difficulty is encountered in deploying the anchoring apparatus, the outer lead portion may be repositioned or even replaced with a different outer lead portion, without removing the guidewire from its position. Secure access to the target site may thereby be maintained throughout the procedure.

This configuration has a further advantage in that the second, inner lead component may be conveniently replaced through the first, outer lead component in the event that the second lead component fails. Moreover, the inner lead component carrying the sensor may even be replaced, even at a much later time, if, for example, a new and more advanced sensor becomes available through further development.

As will be described in more detail below, the system includes circuitry and signaling means that will require power from a compact battery located inside the housing. Those skilled in the art will appreciate that the device may thus require periodic explantation so the battery may be refreshed, or more usually so that the entire unit comprising the housing, the battery, and the internal circuitry can be replaced with a new unit. Nevertheless, it should be possible to leave the device in place inside the patient's body for extended periods comparable to those experienced in connection with pacemakers and implantable defibrillators, and implantation for such extended periods is described in this document as being substantially "permanent."

Figure 9:
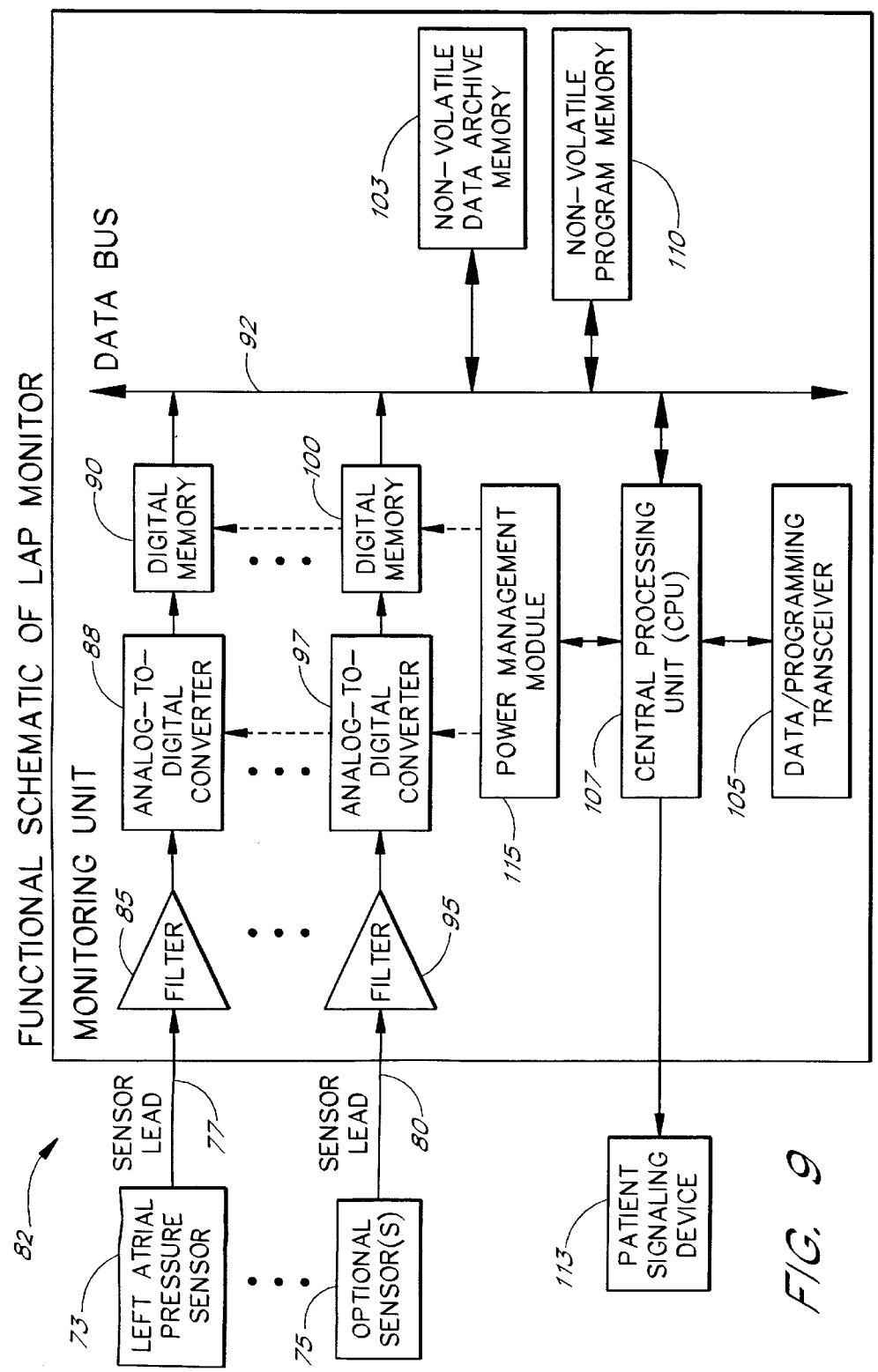
FIG. 9 is a schematic diagram depicting digital circuitry suitable for use in the invention.

The function and operation of the apparatus housed inside the housing will now be described. FIG. 9 is a schematic diagram of operational circuitry located inside the housing 7 and suitable for use with the invention. The apparatus depicted in FIG. 9 includes digital processors, but the same concept could also be implemented with analog circuitry.

As described above, the system of the invention includes a pressure transducer 73 permanently implanted to monitor fluid pressure within the left atrium of the patient's heart. The system may, moreover, include one or more additional sensors 75 configured to monitor pressure at a location outside the left atrium, or a different physical parameter inside the left atrium or elsewhere. For each sensor, a sensor lead 77 and 80 conveys signals from the sensor to a monitoring unit 82 disposed inside the housing of the unit. It should also be noted that the sensor lead connecting the pressure transducer to the monitoring apparatus might also be combined with or run parallel to another lead such as an electrical EKG sensor lead or a cardiac pacing lead, either of which might be placed in or near the left atrium.

When the signal from the left atrial pressure transducer 73 enters the monitoring unit 82, the signal is first passed through a low-pass filter 85 to smooth the signal and reduce noise. The signal is then transmitted to an analog-to-digital converter 88, which transforms the signals into a stream of digital data values, which are in turn stored in digital memory 90. From the memory, the data values are transmitted to a data bus 92, along which they are transmitted to other components of the circuitry to be processed and archived. An additional filter 95, analog-to-digital converter 97, and digital memory area 100 may be provided as shown for each optional sensor 75 whenever such a sensor is present.

From the data bus 92, the digital data are stored in a non-volatile data archive memory area 103. This archive stores the data for later retrieval, for example, by a physician at the patient's next regularly scheduled office visit. The data may be retrieved, for example, by transcutaneous telemetry through a transceiver 105 incorporated into the unit. The same transceiver may serve as a route for transmission of signals into the unit, for example, for reprogramming the unit without explanting it from the patient. The physician may thereby develop, adjust, or refine operation of the unit, for example, as new therapies are developed or depending on the history and condition of any individual patient. Means for transcutaneous signal transmission are known in the art in connection with pacemakers and implantable cardiac defibrillators, and the transceiver used in the present invention may be generally similar to such known apparatus.

The digital data indicative of the pressure detected in the left atrium, as well as data corresponding to the other conditions detected by other sensors, where such are included, are transferred via the data bus 92 into a central processing unit 107, which processes the data based in part on algorithms and other data stored in non-volatile program memory 110. The central processing unit then, based on the data and the results of the processing, sends an appropriate command to a patient signaling device 113, which sends a signal understandable by the patient and based upon which the patient may take appropriate action such as maintaining or changing the patient's drug regimen or contacting his or her physician.

The patient signaling device 113 may be a mechanical vibrator housed inside the housing of the system, a device for delivering a small, harmless, but readily noticeable electrical shock to the patient, or in some embodiments, a low power transmitter configured to transmit information transcutaneously to a remote receiver, which would include a display screen or other means for communicating instructions to the patient. The system may also include apparatus, e.g., cellular or land-line telephone equipment or a device connected to the Internet, for communicating information back to a base location. This could be used, for example, to transmit information concerning the patient's condition back to a hospital or doctor's office, or to transmit information concerning the patient's prescription usage back to a pharmacy.

The circuitry of the invention may also include a power management module 115 configured to power down certain components of the system, e.g., the analog-to-digital converters 88 and 97, digital memories 90 and 100, and the central processing unit 107, between times when those components are in use. This helps to conserve battery power and thereby extend the useful life of the device so that it can remain operational inside the patient's body for extended periods between maintenance or replacement. Other circuitry and signaling modes may be devised by one skilled in the art.

Exemplary modes of operation for the system of the invention will now be described. The system may be programmed, for example, to power up once per hour to measure the left atrial pressure and other conditions as dictated by the configuration of the particular system and any other sensors that might be present. Left atrial pressure measurements are taken at a twenty hertz sampling rate for sixty seconds, yielding 1200 data values reflective of the fluid pressure within the left atrium. The central processing unit then computes the mean left atrial pressure based on the stored values. Then, if the mean pressure is above a threshold value predetermined by the patient's physician, the central processing unit causes an appropriate communication to be sent to the patient via the patient signaling device.

A set of coded communications to the patient can be devised by the treating physician and encoded into the device either at the time of implantation or after implantation by transcutaneous programing using data transmission into the non-volatile program memory 110 via the transceiver 105. For example, assume that the physician has determined that a particular patient's mean left atrial pressure can be controlled at between 15 and 20 mm Hg under optimal drug therapy. This optimal drug therapy might have been found to comprise a drug regimen including 5 milligrams (mg) of Lisinopril, 40 mg of Lasix, 20 milliequivalents (mEq) of potassium chloride, 0.25 mg of Digoxin, and 25 milligrams of Carvedilol, all taken once per twenty-four hour day.

The patient is implanted with the device and the device is programmed as follows. Assume that the device includes a single pressure transducer 73 (see FIG. 9) implanted across the atrial septum inside the patient's left atrium, that the device's programming provides for four possible "alert levels" that are specified according to mean left atrial pressures detected by the transducer and computed in the central processing unit 107, and that the patient signaling device 113 is a mechanical vibrator capable of producing pulsed vibrations readily discernable by the patient.

At predetermined intervals, perhaps hourly, the device measures the patient's mean left arterial pressure as described above, and determines the appropriate alert level for communication to the patient according to programming specified by the physician. For example, a mean left atrial pressure of less than 15 mm Hg could be indicative of some degree of over-medication and would correspond to alert level one. A pressure between 15 and 20 mm Hg would indicate optimal therapy and correspond to alert level two. A pressure between 20 and 30 mm Hg would indicate mild under-treatment or mild worsening in the patient's condition, and would correspond to alert level three. Finally, a mean left atrial pressure above 30 mm Hg would indicate a severe worsening in the patient's condition, and would correspond to alert level four.

When the proper alert level is determined, the device sends a two-second vibration pulse to notify the patient that the device is about to communicate an alert level through a sequence of further vibrations. A few seconds later, a sequence of one to four relatively short (one second) vibratory pulses, the number corresponding to the applicable alert level, are made by the device and felt by the patient. The patient can easily count the pulses to determine the alert level, then continue or modify his own therapy with reference to a chart or other instructions prepared for him by the physician.

For example, two pulses would correspond to alert level two, an optimal or near optimal condition for that particular patient. In that case, the doctor's instructions would tell the patient to continue his or her therapy exactly as before. The signal for alert level two would be given once every 24 hours, at a fixed time each day. This would serve mainly to reassure the patient that the device is working and all is well with his therapy, and to encourage the patient to keep taking the medication on a regular schedule.

One pulse, in contrast, would correspond to alert level one, and most likely some degree of recent over-medication. The doctor's orders would then notify the patient to reduce or omit certain parts of his therapy until the return of alert level two. For example, the doctor's instructions might tell the patient temporarily to stop taking Lasix, and to halve the dosage of Lisinopril to 2.5 mg per day. The coded signal would be given to the patient once every twelve hours until the return of the alert level two condition.

Three pulses would indicate alert level three, a condition of mild worsening in the patient's condition. Accordingly, the doctor's instructions would notify the patient to increase the diuretic components of his therapy until alert level two returned. For example, the patient might be instructed to add to his to his normal doses an additional 80 mg of Lasix, twice daily, and 30 mEq of potassium chloride, also twice daily. The level three alert signal would be given every four hours until the patient's condition returned to alert level two.

Four pulses would indicate alert level four, indicating a serious deterioration in the patient's condition. In this case, the patient would be instructed contact his physician and to increase his doses of diuretics, add a venodilator, and discontinue the beta-blocker. For example, the patient might be instructed to add to his therapy an additional 80 mg of Lasix, twice daily, an additional 30 mEq of potassium chloride, twice daily, 60 mg of Imdur, twice daily, and to stop taking the beta-blocker, Carvedilol. The signal corresponding to alert level four would be given every two hours, or until the physician was able to intervene directly.

Apparatus as described herein may also be useful in helping patients comply with their medication schedule. In that case, the patient signaling device would be programed to signal the patient each time the patient is to take medication, e.g., four times daily. This might be done via an audio or vibratory signal as described above. In versions of the apparatus where the patient signaling device includes apparatus for transmitting messages to a hand held device, tabletop display, or another remote device, written or visual instructions could be provided. Apparatus could also be devised to generate spoken instructions, for example, synthesized speech or the actual recorded voice of the physician, to instruct the patient regarding exactly what medication is to be taken and when.

Where the system includes apparatus for communicating information back to a base location, e.g., the hospital, doctor's office, or a pharmacy, the system could be readily adapted to track the doses remaining in each prescription and to reorder automatically as the remaining supply of any particular drug becomes low.

Advanced embodiments and further refinements of the invention may incorporate sensors in addition to the left atrial pressure sensor. This gives rise to the possibility of further refined diagnostic modes capable of distinguishing between different potential causes of worsening CHF, and then of signaling an appropriate therapeutic treatment depending upon the particular cause for any particular occurrence.

For example, increased left atrial pressure is commonly caused by improper administration of medication, patient non-compliance, or dietary indiscretion, e.g., salt binging. These causes will be generally well-handled by changes in the patient's drug regimen like those described above.

There are other causes of increased left atrial pressures that are less common, but by no means rare, and which require different therapies for adequate treatment. For example, one such potential cause is cardiac arrhythmia, and especially atrial fibrillation with a rapid ventricular response. Other arrythmias may contribute as well to worsening heart failure. A system including an ECG electrode in addition to the left atrial pressure sensor would allow the system to diagnose arrythmias and determine whether the arrhythmia preceded or came after the increase in left atrial pressure. Depending on the unit's programming, as specified by the patient's physician, specific therapies could be signaled tailored to treat the specific causes and conditions associated with particular adverse events.

Although the pressure transducer in the preferred embodiment produces an electrical signal indicative of pressures in its vicinity and, accordingly, an electrical lead is used to transmit the signals to the electronic circuitry, other types of pressure transducers may find use as well. For example, the pressure transducer and lead might comprise a tube filled with an incompressible fluid leading from the left atrium back to a transducer in the housing or at another location. Signals in the form of pressures in the incompressible fluid would then indicate pressures in the left atrium and those pressures would in turn be sensed by the transducer and utilized by the electronic circuitry in generating signals indicative of appropriate therapeutic treatments. Signals in other forms may be used as well and may be transmitted, for example, by fiber optic means, or by any other suitable electrical, electro-mechanical, mechanical, chemical, or other mode of signal transmission.

Moreover, although the signal lead in the preferred embodiment is of an appropriate length so that the housing containing the electronic circuitry can be implanted in the region of the patient's shoulder, the lead may in alternative embodiments be of virtually any useful length, including zero. It may be that an integrated unit might be used in which the pressure transducer is disposed directly on the housing and the entire device implanted inside or very near to the left atrium of the patient's heart.

Certain presently preferred embodiments of apparatus and methods for practicing the invention have been described herein in some detail and some potential modifications and additions have been suggested. Other modifications, improvements and additions not described in this document may also be made without departing from the principles of the invention. Therefore, the full scope of the invention must be ascertained by reference to the appended claims, along with the full scope of equivalents to which those claims are legally entitled.

What is claimed is:

1. Apparatus for treating congestive heart failure in a medical patient, the apparatus comprising:
    a pressure transducer operable to generate a signal indicative of fluid pressure within the left atrium;
    signal processing apparatus operable to generate a signal indicative of an appropriate therapeutic treatment based at least in part on the signal generated by the pressure transducer; and
    a patient signaling device operable to communicate the signal indicative of the appropriate therapeutic treatment to the patient, wherein the patient signaling device is operable to generate at least two distinct signals distinguishable from one another by the patient, each said signal indicative of a different therapeutic treatment.

2. The apparatus of claim 1, further comprising an implantable flexible lead providing a signal connection between the pressure transducer and the signal processing apparatus.

3. The apparatus of claim 2, further comprising apparatus on the lead configured to anchor pressure transducer to the patient's atrial septum.

4. The apparatus of claim 2, wherein the pressure transducer is located on the lead a predetermined distance away from a distal tip of the lead, wherein the distance is predetermined so that the pressure transducer will be positioned within the patient's left atrium when the distal tip is positioned within a pulmonary vein connected to the patient's left atrium.

5. The apparatus of claim 2, wherein the lead comprises a first lead component carrying apparatus configured to anchor the first lead component to the patient's atrial septum and a second lead component carrying the pressure transducer, wherein the second lead component is implantable into the patient and fixable to the first lead component after the first lead component is implanted within the patient.

6. The apparatus of claim 3, wherein the apparatus on the lead configured to anchor the pressure transducer to the patient's atrial septum comprises a helical screw configured for advancement into and fixation within the atrial septum.

7. The apparatus of claim 3, wherein the apparatus on the lead configured to anchor the pressure transducer to the patient's atrial septum comprises at least one anchor deployable by spring force upon the withdrawal of a removable sheath to expose the anchor.

8. The apparatus of claim 1, wherein the signal processing apparatus is at least partially contained within a housing, the housing configured for permanent implantation within the patient's body.

9. The apparatus of claim 1, further comprising apparatus configured to anchor the pressure transducer to the patient's atrial septum.

10. The apparatus of claim 1, wherein the signal processing apparatus includes an analog-to-digital converter operable to convert analog signals from the pressure transducer to digital data reflective of the fluid pressure within the left atrium.

11. The apparatus of claim 1, wherein the signal processing apparatus includes digital memory for storing data reflective of pressures within the left atrium.

12. The apparatus of claim 11, further comprising apparatus configured to retrieve the data reflective of pressures within the left atrium from the digital memory.

13. The apparatus of claim 12, wherein the data retrieval apparatus includes a transceiver operable to transmit the data through the patient's skin.

14. The apparatus of claim 1, wherein the signal processing apparatus is operable to receive modified programming with the signal processing apparatus implanted within the patient's body.

15. The apparatus of claim 1, wherein the patient signaling device includes apparatus configured to produce an electrical shock perceptible by the patient.

16. The apparatus of claim 1, wherein the patient signaling device is operable to generate at least four distinct signals distinguishable from one another by the patient, each said signal indicative of a different therapeutic treatment.

17. An apparatus according to claim 1, wherein the transducer is situated within the left atrium.

18. An apparatus according to claim 1, wherein the transducer is situated within a pulmonary vein.

19. An apparatus according to claim 1, wherein the transducer is situated within the left atrial appendage.

20. An apparatus according to claim 1, wherein the transducer is located in the septal wall.

21. An apparatus according to claim 1, wherein the transducer is situated at a location within the heart having a pressure that is at least nearly the same as the pressure in the left atrium.

22. An apparatus according to claim 1, wherein the transducer is situated at a location within the heart sufficient to generate a signal indicative of fluid pressure within the left atrium.

23. An apparatus according to claim 1, wherein the transducer is situated at a location outside the heart sufficient to generate a signal indicative of fluid pressure within the left atrium.

24. An apparatus according to claim 1, wherein the transducer is situated at a location relative to the heart sufficient to generate a signal indicative of fluid pressure within the left atrium.

25. An apparatus according to claim 1, wherein the transducer is associated with the heart in a manner that is sufficient to generate a signal indicative of fluid pressure within the left atrium.

26. An The apparatus of claim 1, further comprising a second sensor in addition to the pressure transducer, the second sensor operable to generate a second signal indicative of a second condition within the body of the patient, wherein the signal processing apparatus is operable to generate a signal indicative of an appropriate therapeutic treatment based at least in part on the second signal generated by the sound sensor.

27. The apparatus of claim 26, wherein the second sensor is a second pressure transducer.

28. The apparatus of claim 26, wherein the second sensor is an ECG electrode.

29. The apparatus of claim 26, wherein the second sensor is configured for implantation in the patient's right atrium.

30. The apparatus of claim 26, wherein the second sensor is configured for implantation in a location inside the patient's body outside the atria.

31. The apparatus of claim 1, wherein the patient signaling device includes a mechanical vibrator operable to produce a vibration perceptible by the patient.

32. The apparatus of claim 1, wherein the patient signaling device includes a transmitter operable to send information to a remote receiver.

33. The apparatus of claim 1, wherein the signal processing apparatus includes power management circuitry operable to deny power to at least some portions of the signal processing apparatus during periods of relative inactivity between periods of device operation.

34. The apparatus of claim 1, wherein the signal processing apparatus includes apparatus operable to compute mean left atrial pressures based on multiple individual signals generated by the pressure transducer.

35. The apparatus of claim 1, wherein the patient signaling device is operable to generate at least one signal indicative of an appropriate therapeutic treatment comprising a reduction in the normal dose of at least one medication taken by the patient.

36. The apparatus of claim 1, wherein the patient signal device generates signals in the form of predetermined sequences of individual signal pulses, the signal pulses being perceptible by the patient.

37. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; and a patient signaling device operable to communicate the signal indicative of the appropriate therapeutic treatment to the patient;

an implantable flexible lead providing a signal connection between the pressure transducer and the signal processing apparatus; and apparatus on the lead configured to anchor the pressure transducer to the patient's atrial septum comprising a helical screw configured for advancement into and fixation within the atrial septum.

38. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer;

a patient signaling device operable to communicate the signal indicative of the appropriate therapeutic treatment to the patient;

an implantable flexible lead providing a signal connection between the pressure transducer and the signal processing apparatus; and apparatus on the lead configured to anchor the pressure transducer to the patient's atrial septum comprising at least one anchor deployable by spring force upon the withdrawal of a removable sheath to expose the anchor.

39. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer;

a patient signaling device operable to communicate the signal indicative of the appropriate therapeutic treatment to the patient; and an implantable flexible lead providing a signal connection between the pressure transducer and the signal processing apparatus, wherein the pressure transducer is located on the lead a predetermined distance away from a distal tip of the lead, wherein the distance is predetermined so that the pressure transducer will be positioned within the patient's left atrium when the distal tip is positioned within a pulmonary vein connected to the patient's left atrium.

40. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer;

a patient signaling device operable to communicate the signal indicative of the appropriate therapeutic treatment to the patient;

an implantable flexible lead providing a signal connection between the pressure transducer and the signal processing apparatus, wherein the lead comprises a first lead component carrying apparatus configured to anchor the first lead component to the patient's atrial septum and a second lead component carrying the pressure transducer, wherein the second lead component is implantable into the patient and fixable to the first lead component after the first lead component is implanted within the patient.

41. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer;

a patient signaling device operable to communicate the signal indicative of the appropriate therapeutic treatment to the patient; and a second sensor in addition to the pressure transducer, the second sensor operable to generate a second signal indicative of a second condition within the body of the patient, wherein the signal processing apparatus is operable to generate a signal indicative of an appropriate therapeutic treatment based at least in part on the second signal generated by the second sensor.

42. The apparatus of claim 41, wherein the second sensor is a second pressure transducer.

43. The apparatus of claim 41, wherein the second sensor is an ECG electrode.

44. The apparatus of claim 41, wherein the second sensor is configured for implantation in the patient's right atrium.

45. The apparatus of claim 41, wherein the second sensor is configured for implantation in a location inside the patient's body outside the atria.

46. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; wherein the signal processing apparatus includes digital memory for storing data reflective of pressures within the left atrium;

a patient signaling device operable to communicate the signal indicative of the appropriate therapeutic treatment to the patient; and apparatus configured to retrieve the data reflective of pressures within the left atrium from the digital memory, wherein the data retrieval apparatus includes a transceiver operable to transmit the data through the patient's skin.

47. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; and a patient signaling device operable to communicate the signal indicative of the appropriate therapeutic treatment to the patient, wherein the patient signaling device includes a mechanical vibrator operable to produce a vibration perceptible by the patient.

48. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; and a patient signaling device operable to communicate the signal indicative of the appropriate therapeutic treatment to the patient, wherein the patient signaling device includes a transmitter operable to send information to a remote receiver.

49. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer, wherein the signal processing apparatus includes power management circuitry operable to deny power to at least some portions of the signal processing apparatus during periods of relative inactivity between periods of device operation; and a patient signaling device operable to communicate the signal indicative of the appropriate therapeutic treatment to the patient.

50. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer, wherein the signal processing apparatus includes apparatus operable to compute mean left atrial pressures based on multiple individual signals generated by the pressure transducer; and a patient signaling device operable to communicate the signal indicative of the appropriate therapeutic treatment to the patient.

51. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; and a patient signaling device operable to communicate the signal indicative of the appropriate therapeutic treatment to the patient, wherein the patient signaling device is operable to generate at least one signal indicative of an appropriate therapeutic treatment comprising a reduction in the normal dose of at least one medication taken by the patient.

52. Apparatus for treating congestive heart failure in a medical patient, the apparatus comprising:

a pressure transducer operable to generate a signal indicative of fluid pressure within the left atrium;

signal processing apparatus operable to generate a signal indicative of an appropriate therapeutic treatment based at least in part on the signal generated by the pressure transducer; and a patient signaling device operable to communicate the signal indicative of the appropriate therapeutic treatment to the patient, wherein the patient signal device generates signals in the form of predetermined sequences of individual signal pulses, the signal pulses being perceptible by the patient.

53. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment, wherein operating the signal processing apparatus includes generating one of at least two distinct signals, each said signal indicative of a different therapeutic treatment; and communicating the signal indicative of the appropriate therapeutic treatment to the patient.

54. The method of claim 53, and further comprising implanting at least a portion of the signal processing apparatus substantially permanently within the patient's body.

55. The method of claim 53, and further comprising anchoring the pressure transducer to the patient's atrial septum.

56. The method of claim 55, wherein implanting the signal processing apparatus within the patient's body includes implanting the signal processing apparatus a subcutaneous pocket in the region of the patient's shoulder.

57. The method of claim 55, wherein anchoring the pressure transducer to the patient's atrial septum comprises advancing a helical screw into the patient's atrial septum.

58. The method of claim 55, wherein anchoring the pressure transducer to the patient's atrial septum comprises withdrawing a removable sheath to deploy at least one anchor by spring force to bear against the patient's atrial septum.

59. The method of claim 53, and further comprising implanting the signal processing apparatus within the patient's body.

60. The method of claim 53, wherein communicating the signal indicative of the appropriate therapeutic treatment includes generating an electrical shock perceptible by the patient.

61. The method of claim 53, wherein generating one of at least two distinct signals, each said signal indicative of a different therapeutic treatment, includes generating one of at least four distinct signals.

62. A apparatus according to claim 53, wherein the transducer is situated within the left atrium.

63. An apparatus according to claim 53, wherein the transducer is situated within a pulmonary vein.

64. An apparatus according to claim 53, wherein the transducer is situated within the left atrial appendage.

65. An apparatus according to claim 53, wherein the transducer is located in the septal wall.

66. An apparatus according to claim 53, wherein the transducer is situated at a location within the heart having a pressure that is at least nearly the same as the pressure in the left atrium.

67. An apparatus according to claim 53, wherein the transducer is situated within the heart.

68. An apparatus according to claim 53, wherein the transducer is situated outside of the heart.

69. An apparatus according to claim 53, wherein the transducer is associated with the heart in a manner that is sufficient to generate a signal indicative of fluid pressure within the left atrium.

70. A apparatus according to claim 53, wherein the transducer is situated within the left atrium.

71. The method of claim 53, wherein implanting a pressure transducer within the left atrium of the patient's heart comprises:

approaching the left atrium through the right atrium;

penetrating the patient's atrial septum; and positioning the pressure transducer in side the patient's left atrium.

72. The method of claim 71, and further comprising approaching the right atrium through the superior vena cava.

73. The method of claim 71, and further comprising approaching the right atrium through the inferior vena cava.

74. The method of claim 53, wherein implanting the pressure transducer substantially permanently within the left atrium of the patient's heart includes advancing a flexible lead carrying the pressure transducer partially into a pulmonary vein connected to the left atrium while positioning the pressure transducer within the left atrium.

75. The method of claim 53, wherein implanting the pressure transducer substantially permanently within the left atrium of the patient's heart includes:

advancing a first lead component carrying anchoring apparatus to the left atrium and deploying the anchoring apparatus to anchor the first lead component to the patient's atrial septum; and advancing a second lead component carrying a pressure transducer along the first lead component until the second lead component is in a position wherein the pressure transducer is positioned within the patient's left atrium.

76. The method of claim 53, wherein communicating the signal indicative of the appropriate therapeutic treatment includes operating a mechanical vibrator to produce a vibration perceptible by the patient.

77. The method of claim 53, wherein communicating the signal indicative of the appropriate therapeutic treatment includes operating a transmitter to send information to a remote receiver.

78. The method of claim 53, further comprising operating power management circuitry to deny power to at least some portions of the signal processing apparatus during periods of relative inactivity between periods of active operation of those portions of the signal processing apparatus.

79. The method of claim 53, wherein operating the signal processing apparatus to generate a signal indicative of an appropriate therapeutic treatment includes computing mean left atrial pressures based on multiple individual signals generated by the pressure transducer.

80. The method of claim 53, wherein operating the signal processing apparatus to generate a signal indicative of an appropriate therapeutic treatment includes generating a signal indicative of an appropriate therapeutic treatment comprising a reduction in the normal dose of at least one medication taken by the patient.

81. The method of claim 53, wherein communicating the signal indicative of the appropriate therapeutic treatment to the patient includes communicating to the patient at least one predetermined sequence comprising multiple individual signal pulses perceptible by the patient.

82. The method of claim 53, wherein operating wherein operating the signal processing apparatus to generate a signal indicative of an appropriate therapeutic treatment includes diagnosing a cause of worsening CHF.

83. A method for treating congestive heart failure in a medical patient, the method comprising:
   implanting a pressure transducer substantially permanently within the left atrium of the patient's heart, wherein implanting the pressure transducer within the left atrium of the patient's heart comprises:
   approaching the left atrium through the right atrium;
   penetrating the patient's atrial septum; and
   positioning the pressure transducer in side the patient's left atrium;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment; and
   communicating the signal indicative of the appropriate therapeutic treatment to the patient.

84. The method of claim 83, and further comprising approaching the right atrium through the superior vena cava.

85. The method of claim 83, and further comprising approaching the right atrium through the inferior vena cava.

86. A method for treating congestive heart failure in a medical patient, the method comprising:
   implanting a pressure transducer substantially permanently within the left atrium of the patient's heart;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment;
   communicating the signal indicative of the appropriate therapeutic treatment to the patient; and
   anchoring the pressure transducer to the patient's atrial septum, by advancing a helical screw into the patient's atrial septum.

87. A method for treating congestive heart failure in a medical patient, the method comprising:
   implanting a pressure transducer substantially permanently within the left atrium of the patient's heart;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment;
   communicating the signal indicative of the appropriate therapeutic treatment to the patient; and
   withdrawing a removable sheath to deploy at least one anchor by spring force to bear against the patient's atrial septum, thereby anchoring the pressure transducer to the patient's atrial septum.

88. A method for treating congestive heart failure in a medical patient, the method comprising:
   implanting a pressure transducer substantially permanently within the left atrium of the patient's heart, wherein said implanting includes advancing a flexible lead carrying the pressure transducer partially into a pulmonary vein connected to the left atrium while positioning the pressure transducer within the left atrium;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment; and
   communicating the signal indicative of the appropriate therapeutic treatment to the patient.

89. A method for treating congestive heart failure in a medical patient, the method comprising:
   implanting a pressure transducer substantially permanently within the left atrium of the patient's heart, wherein said implanting includes:
      advancing a first lead component carrying anchoring apparatus to the left atrium and deploying the anchoring apparatus to anchor the first lead component to the patient's atrial septum; and
      advancing a second lead component carrying a pressure transducer along the first lead component until the second lead component is in a position wherein the pressure transducer is positioned within the patient's left atrium;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment; and
   communicating the signal indicative of the appropriate therapeutic treatment to the patient.

90. A method for treating congestive heart failure in a medical patient, the method comprising:
   implanting a pressure transducer substantially permanently within the left atrium of the patient's heart;
   operating the pressure transducer to generate a signal indicative of fluid pressure within the left atrium;
   communicating the signal indicative of the fluid pressure within the left atrium to signal processing apparatus;
   operating the signal processing apparatus to generate a signal indicative of an appropriate therapeutic treatment; and
   communicating the signal indicative of the appropriate therapeutic treatment to the patient, wherein said communicating includes operating a mechanical vibrator to produce a vibration perceptible by the patient.

91. A method for treating congestive heart failure in a medical patient, the method comprising:
   implanting a pressure transducer substantially permanently within the left atrium of the patient's heart;
   operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment; and communicating the signal indicative of the appropriate therapeutic treatment to the patient, wherein said communicating includes operating a transmitter to send information to a remote receiver.

92. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment;

communicating the signal indicative of the appropriate therapeutic treatment to the patient; and operating power management circuitry to deny power to at least some portions of the signal processing apparatus during periods of relative inactivity between periods of active operation of those portions of the signal processing apparatus.

93. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment, wherein said operating includes computing mean left atrial pressures based on multiple individual signals generated by the pressure transducer; and communicating the signal indicative of the appropriate therapeutic treatment to the patient.

94. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment, wherein said operating includes generating a signal indicative of an appropriate therapeutic treatment comprising a reduction in the normal dose of at least one medication taken by the patient; and communicating the signal indicative of the appropriate therapeutic treatment to the patient.

95. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment; and communicating the signal indicative of the appropriate therapeutic treatment to the patient, wherein communicating the signal includes communicating to the patient at least one predetermined sequence comprising multiple individual signal pulses perceptible by the patient.

96. A method for treating congestive heart failure in a medical patient, the method comprising:

implanting a pressure transducer substantially permanently within the left atrium of the patient's heart;

operating the pressure transducer to generate a signal indicative of fluid pressure within the left atrium;

communicating the signal indicative of the fluid pressure within the left atrium to signal processing apparatus;

operating the signal processing apparatus to generate a signal indicative of an appropriate therapeutic treatment, wherein operating the signal processing apparatus includes diagnosing a cause of worsening CHF; and communicating the signal indicative of the appropriate therapeutic treatment to the patient.

97. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient, wherein the patient signaling device is operable to generate at least two distinct signals distinguishable from one another by the patient, each said signal indicative of a different therapeutic treatment.

98. An apparatus according to claim 97, wherein the indicator means is a pressure transducer.

99. A apparatus according to claim 97, wherein the indicator means is situated within the left atrium.

100. An apparatus according to claim 97, wherein the indicator means is situated within a pulmonary vein.

101. An apparatus according to claim 97, wherein the indicator means is situated within the left atrial appendage.

102. An apparatus according to claim 97, wherein the indicator means is located in the septal wall.

103. An apparatus according to claim 97, wherein the indicator means is situated at a location within the heart having a pressure that is at least nearly the same as the pressure in the left atrium.

104. An apparatus according to claim 97, wherein the indicator means is situated at a location within the heart sufficient to generate a signal indicative of fluid pressure within the left atrium.

105. An apparatus according to claim 97, wherein the indicator means is situated at a location outside the heart sufficient to generate a signal indicative of fluid pressure within the left atrium.

106. An apparatus according to claim 97, wherein the indicator means is situated at a location relative to the heart sufficient to generate a signal indicative of fluid pressure within the left atrium.

107. An apparatus according to claim 97, wherein the indicator means is associated with the heart in a manner that is sufficient to generate a signal indicative of fluid pressure within the left atrium.

108. The apparatus of claim 97, further comprising an implantable flexible lead providing a signal connection between the indicator means and the signal processing apparatus.

109. The apparatus of claim 108, further comprising apparatus configured to anchor the indicator means to the patient's atrial septum.

110. The apparatus of claim 108, wherein the indicator means is located on the lead a predetermined distance away from a distal tip of the lead, wherein the distance is predetermined so that the indicator means will be positioned within the patient's left atrium when the distal tip is positioned within a pulmonary vein connected to the patient's left atrium.

111. The apparatus of claim 108, wherein the lead comprises a first lead component carrying apparatus configured to anchor the first lead component to the patient's atrial septum and a second lead component carrying the indicator means, wherein the second lead component is implantable into the patient and fixable to the first 5 lead component after the first lead component is implanted within the patient.

112. The apparatus of claim 109, further comprising apparatus on the lead configured to anchor the indicator means to the patient's atrial septum.

113. The apparatus of claim 69, wherein the apparatus configured to anchor the indicator means to the patient's atrial septum comprises a helical screw configured for advancement into and fixation within the atrial septum.

114. The apparatus of claim 69, wherein the apparatus on the lead configured to anchor the indicator means to the patient's atrial septum comprises at least one anchor deployable by spring force upon the withdrawal of a removable sheath to expose the anchor.

115. The apparatus of claim 97, wherein the signal processing apparatus is at least partially contained within a housing, the housing configured for permanent implantation within the patient's body.

116. The apparatus of claim 97, wherein the signal processing apparatus includes an analog-to-digital converter operable to convert analog signals from the indicator means to digital data reflective of the fluid pressure within the left atrium.

117. The apparatus of claim 97, wherein the signal processing apparatus includes digital memory for storing data reflective of pressures within the left atrium.

118. The apparatus of claim 117, further comprising apparatus configured to retrieve the data reflective of pressures within the left atrium from the digital memory.

119. The apparatus of claim 118, wherein the data retrieval apparatus includes a transceiver operable to transmit the data through the patient's skin.

120. The apparatus of claim 97, wherein the signal processing apparatus is operable to receive modified programming with the signal processing apparatus implanted within the patient's body.

121. The apparatus of claim 97, wherein the patient signaling device includes a mechanical vibrator operable to produce a vibration perceptible by the patient.

122. The apparatus of claim 97, wherein the patient signaling device includes apparatus configured to produce an electrical shock perceptible by the patient.

123. The apparatus of claim 69, wherein the patient signaling device is operable to generate at least four distinct signals distinguishable from one another by the patient, each said signal indicative of a different therapeutic treatment.

124. The apparatus of claim 97, wherein the patient signal device generates signals in the form of predetermined sequences of individual signal pulses, the signal pulses being perceptible by the patient.

125. The apparatus of claim 97, further comprising a second sensor in addition to the indicator means, the second sensor operable to generate a second signal indicative of a second condition within the body of the patient, wherein the signal processing apparatus is operable to generate a signal indicative of an appropriate therapeutic treatment based at least in part on the second signal generated by the second sends.

126. The apparatus of claim 97, wherein the patient signaling device includes a transmitter operable to send information to remote receiver.

127. The apparatus of claim 97, wherein the signal processing apparatus includes power management circuitry operable to deny power to at least some portions of the signal processing apparatus during periods of relative inactivity between periods of device operation.

128. The apparatus of claim 97, wherein the signal processing apparatus includes apparatus operable to compute mean left atrial pressures based on multiple individual signals generated by the indicator means.

129. The apparatus of claim 97, wherein the patient signaling device is operable to generate at least one signal indicative of an appropriate therapeutic treatment comprising a reduction in the normal dose of at least one medication taken by the patient.

130. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient;

an implantable flexible lead providing a signal connection between the indicator means and the signal processing apparatus; and apparatus configured to anchor the indicator means to the patient's atrial septum, wherein the apparatus comprises a helical screw configured for advancement into and fixation within the atrial septum.

131. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient;

an implantable flexible lead providing a signal connection between the indicator means and the signal processing apparatus; and apparatus configured to anchor the indicator means to the patient's atrial septum, wherein the apparatus comprises at least one anchor deployable by spring force upon the withdrawal of a removable sheath to expose the anchor.

132. Apparatus for treating congestive heart failure in a medical patient, the apparatus comprising:

indicator means for generating a signal indicative of fluid pressure within the left atrium, wherein the indicator means is located on the lead a predetermined distance away from a distal tip of the lead, wherein the distance is predetermined so that the indicator means will be positioned within the patient's left atrium when the distal tip is positioned within a pulmonary vein connected to the patient's left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient;

an implantable flexible lead providing a signal connection between the indicator means and the signal processing apparatus.

133. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient; and an implantable flexible lead providing a signal connection between the indicator means and the signal processing apparatus, wherein the lead comprises a first lead component carrying apparatus configured to anchor the first lead component to the patient's atrial septum and a second lead component carrying the indicator means, wherein the second lead component is implantable into the patient and fixable to the first lead component after the first lead component is implanted within the patient.

134. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient; and a second sensor in addition to the indicator means, the second sensor operable to generate a second signal indicative of a second condition within the body of the patient, wherein the signal processing apparatus is operable to generate a signal indicative of an appropriate therapeutic treatment based at least in part on the second signal generated by the second sensor.

135. The apparatus of claim 134, wherein the second sensor is a pressure transducer.

136. The apparatus of claim 134, wherein the second sensor is an ECG electrode.

137. The apparatus of claim 134, wherein the second sensor is configured for implantation in the patient's right atrium.

138. The apparatus of claim 134, wherein the second sensor is configured for implantation in a location inside the patient's body outside the atria.

139. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means, wherein the signal processing apparatus includes digital memory for storing data reflective of pressures within the left atrium;

a patient signaling device operable to communicate the signal indicative of the appropriate therapeutic treatment to the patient;

apparatus configured to retrieve the data reflective of pressures within the left atrium from the digital memory; and wherein the data retrieval apparatus includes a transceiver operable to transmit the data through the patient's skin.

140. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means; and a patient signaling device operable to communicate the signal indicative of the appropriate therapeutic treatment to the patient; wherein the patient signaling device includes a transmitter operable to send information to a remote receiver.

141. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means, wherein the signal processing apparatus includes power management circuitry operable to deny power to at least some portions of the signal processing apparatus during periods of relative inactivity between periods of device operation; and a patient signaling device operable to communicate the signal indicative of the appropriate therapeutic treatment to the patient.

142. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means, wherein the signal processing apparatus includes apparatus operable to compute mean left atrial pressures based on multiple individual signals generated by the indicator means; and a patient signaling device operable to communicate the signal indicative of the appropriate therapeutic treatment to the patient.

143. Apparatus for treating congestive heart failure in a medical patient, the apparatus comprising:

indicator means for generating a signal indicative of fluid pressure within the left atrium;

signal processing apparatus operable to generate a signal indicative of an appropriate therapeutic treatment based at least in part on the signal generated by the indicator means, wherein the patient signaling device is operable to generate at least one signal indicative of an appropriate therapeutic treatment comprising a reduction in the normal dose of at least one medication taken by the patient; and a patient signaling device operable to communicate the signal indicative of the appropriate therapeutic treatment to the patient.

* * * * *

UNITED STATES PATENT AND TRADEMARK OFFICE
CERTIFICATE OF CORRECTION

PATENT NO.    : 6,328,699 B1
DATED         : December 11, 2001
INVENTOR(S)   : Neal L. Eigler and James S. Whiting It is certified that error appears in the above-identified patent and that said Letters Patent is hereby corrected as shown below:

Title page,
Item [56], References Cited, U.S. PATENT DOCUMENTS, "5,163,439" should be -- 5,163,429 --

Column 1,
Line 16, please change "hypoxernia" to -- hypoxemia --

Column 3,
Line 1, please change "Elevating" to -- Elevated --
Line 3, please change "Means left atrail" to -- Mean left atrial --
Line 4, please change "in normally" to -- is normally --
Line 7, please change "atrail" to -- atrial --
Line 13, please change "very reliable" to -- very reliably --
Line 15, please change "...heart Thus, the methods..." to -- ...heart. Thus, the methods... --

Column 6,
Line 13, please change "having removed" to -- having been removed --
Line 58, please change "As I the" to -- As in the --

Column 7,
Line 8, delete "to"

Column 13,
Line 38, please change "sound sensor" to -- second sensor --

Column 14,
Lines 15-16, phrase "of the appropriate therapeutic" should be on the same line (no new paragraph)

Column 17,
Line 39, please change "apparatus a subcutaneous" to -- apparatus in a subcutaneous --

Column 18,
Line 20, please change "in side" to -- inside --

UNITED STATES PATENT AND TRADEMARK OFFICE
CERTIFICATE OF CORRECTION

PATENT NO. : 6,328,699 B1
DATED : December 11, 2001
INVENTOR(S) : Neal L. Eigler and James S. Whiting It is certified that error appears in the above-identified patent and that said Letters Patent is hereby corrected as shown below:

Column 19,
Lines 16-19, "approaching the left atrium through the right atrium; penetrating the patient's atrial septum; and positioning the pressure transducer in side the patient's left atrium;" should be indented under line 11.
Line 19, please change "in side" to -- inside --

Column 23,
Line 26, please change "the first 5 lead component" to -- the first lead component --
Line 31, please change "The apparatus of claim 69" to -- The apparatus of claim 109 --
Line 35, please change "The apparatus of claim 69" to -- The apparatus of claim 109 --

Column 24,
Line 1, please change "The apparatus of claim 69" to -- The apparatus of claim 97 --
Line 15, please change "second sends" to -- second sensor --
Line 18, please change "to remote" to -- to a remote --

Signed and Sealed this

First Day of October, 2002

*Attest:*

*Attesting Officer*

JAMES E. ROGAN
*Director of the United States Patent and Trademark Office*